(12) United States Patent
Yasuda et al.

(10) Patent No.: US 7,597,850 B2
(45) Date of Patent: Oct. 6, 2009

(54) DROPLET OPERATION DEVICE

(75) Inventors: Kenji Yasuda, 8-14-1014, Shiomi 2-chome, Koto-ku, Tokyo (JP); Takanori Ichiki, Tokyo (JP); Kazunori Okano, Tokyo (JP)

(73) Assignee: Kenji Yasuda, Tokyo (JP)

( * ) Notice: Subject to any disclaimer, the term of this patent is extended or adjusted under 35 U.S.C. 154(b) by 406 days.

(21) Appl. No.: 10/525,521

(22) PCT Filed: Aug. 26, 2003

(86) PCT No.: PCT/JP03/10761

§ 371 (c)(1),
(2), (4) Date: Aug. 9, 2005

(87) PCT Pub. No.: WO2004/019005

PCT Pub. Date: Mar. 4, 2004

(65) Prior Publication Data

US 2006/0039828 A1 Feb. 23, 2006

(30) Foreign Application Priority Data

Aug. 26, 2002 (JP) .................. 2002-245901

(51) Int. Cl.
*B01L 3/02* (2006.01)

(52) U.S. Cl. .................. 422/100; 422/99; 422/101; 436/180; 204/164

(58) Field of Classification Search ........... 422/99–101; 436/180; 204/164
See application file for complete search history.

(56) References Cited

U.S. PATENT DOCUMENTS 5,066,512 A * 11/1991 Goldowsky et al. ......... 427/466

5,486,337 A * 1/1996 Ohkawa ................. 422/100
5,849,486 A * 12/1998 Heller et al. ............... 435/6
6,589,739 B2 * 7/2003 Fisher .................... 506/32

FOREIGN PATENT DOCUMENTS

JP 11-218691 8/1999

(Continued)

OTHER PUBLICATIONS

Takanori Ichiki, "Biological Analysis Chips Fabricated by Micro/Nano Fabrication Technologies", vol. 19, No. 3, Mar. 12, 2002, pp. 39-45, (with English translation).

(Continued)

*Primary Examiner*—Jill Warden
*Assistant Examiner*—Jyoti Nagpaul
(74) *Attorney, Agent, or Firm*—Wenderoth, Lind & Ponack, L.L.P.

(57) ABSTRACT

A droplet operation device has a substrate with light transmissibility and having been subjected to a water repellent treatment, a way for supplying droplets onto the substrate, a way for transporting the droplets on the water repellent substrate, and a way for measuring the state of the droplets. The droplet operation device includes the light transmittable substrate, solvent feeding ports for leading reagent or specimen droplets onto the substrate, optical measuring units, and electric field application units. As a result, the inside of the droplets can be observed with a microscope, and results of the reaction of the droplets against other droplets can be measured and classified by stopping and moving the droplets in any direction.

10 Claims, 2 Drawing Sheets

FOREIGN PATENT DOCUMENTS

JP 2001-38246 2/2001
JP 2003-107099 4/2003

OTHER PUBLICATIONS

Ujiie, Hara et al., "Study of Cell Sorter Chips using Dielectrophoretic Force", separate vol. 3, Mar. 28, 2001, p. 1276, 29p-R-6, (with English translation).

Hara, Ichiki et al.; "Development of Cell Sorter Chips Using Dielectrophoretic Force[II]", the Japan Society of Applied Physics, separate vol. 3, Sep. 11, 2001, p. 975, 11a-ZA-2, (with English translation).

* cited by examiner

DROPLET OPERATION DEVICE

TECHNICAL FIELD

The present invention relates to a new device for operating droplets.

BACKGROUND ART

Separating and recovering specified cells in a culture solution is very important technique in biological and medical analyses. Normally, when cells are sorted according to differences in their specific gravity, the sorting can be carried out by a velocity sedimentation method. When, however, differences in cells such as distinguishing unsensitized cells from sensitized cells are hardly present, it is necessary to sort the cells one by one based on information obtained either by staining with a fluorescent antibody or by visual observation. This technique includes, for example, cell sorters. Each individual, fluorescently stained cell is isolated into a liquid drop to which an electric charge is imparted. Based on the presence or absence of fluorescence from the cell in the liquid drop or based on the amount of scattering light, a high electric field is applied in an arbitrary direction perpendicular to the direction of dropping while the drop is falling to thereby control the direction of dropping of the liquid drop. In this way, the cells are separately recovered in a plurality of containers placed underneath. The details of this technique are reported in "Methods Enzymol, Vol. 151, pp. 150 to 165 (1987)" by Kamarck. M. E.

SUMMARY OF INVENTION

The cell fractionating technique using the conventional sorters enables observation based on optical information by unit of droplet that is conventionally impossible; and it is difficult to optically and microscopically observe internal states of droplets which drop freely. Particularly, a method of directly checking whether a drop actually includes only one cell is not present, and an electric field can only be applied to a normal plane direction of a dropping droplet. For this reason, only a dropping angle of liquid can be basically adjusted. Further, in order to sufficiently deflect an angle of a droplet dropping at a high speed for a short time, it is necessary to apply a high electric field of not less than 2000 V. The conventional cell sorters can make a measurement only once; and after the reaction liquid is mixed with a fractionated droplet, the cell sorters cannot segregate cells according to the mixed result.

It is, therefore, an object of the present invention to provide a new droplet operation device which solves the conventional technical problems, enables observation of the inside of a droplet including cell or microbe, keeps the droplet at rest and can move it to any direction, optically measures one droplet a plurality of times, reacts a droplet with another droplet so as to measure the reacted result, and can fractionate the droplet.

The present invention provides the droplet operation device in which the above problems are solved and a plurality of electrodes are arranged on an insulating substrate whose surface is subject to water repellent treatment. The droplet operation device includes: a unit for supplying a droplet onto the substrate; a unit for applying a DC or AC field to the electrodes so as to carry the droplet on the water-repelled substrate; and a unit for measuring a state of the droplet.

Further, the present invention provides for the droplet operation device to include a unit for measuring pH, ion density, absorbance, fluorescence and the like of the droplet using optical imaging, an optical sensor or the like by means of a microscope as a unit for measuring the state of the droplet. The invention further provides for the droplet operation device to have a unit for mixing a plurality of droplets.

BEST MODES FOR CARRYING OUT THE INVENTION

The present invention has the above-mentioned characteristics, but an embodiment is explained below.

Figure 1:
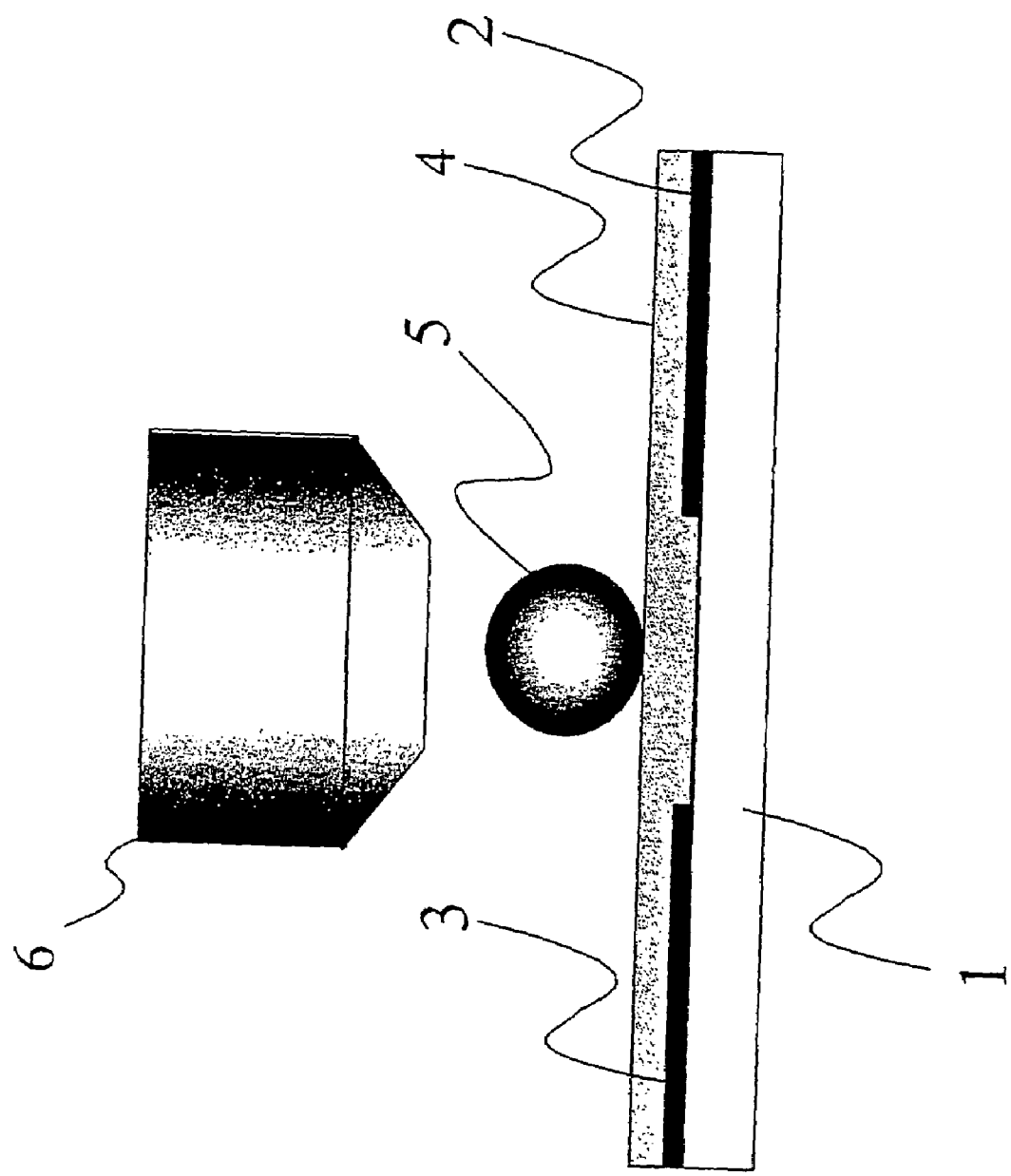
FIG. 1 is a pattern diagram illustrating a basic constitution of the present invention.

A basic constitution of a droplet operation device according to the present invention is explained with reference to FIG. 1. In this embodiment, an insulating layer 4 is arranged so as to cover a plurality of electrodes 2 and 3 arranged on an insulating substrate 1. The surface of the insulating layer 4 is subject to water repellent treatment, and the water repellent treatment in this case may be given in any suitable manner. Various methods including a method of coating the surface with silicon resin or fluorocarbon resin, and a method of forming an uneven surface having a fractal structure on the surface of the substrate so as to give a water repellent property thereto may be considered.

A droplet 5 including a cell and microbe is held in a spherical state on the substrate. When electric charges are applied to the droplet, like a cell sorter, a DC field is applied to the electrodes 2 and 3 so that a moving direction of the droplet can be controlled. In the case of a droplet to which an electric charge is not applied, for example, a DC field is applied between the electrodes 2 and 3 so that cell or microbe can be moved. In order to observe the cell in the droplet, the state of the cell or microbe in the droplet can be directly observed in a phase contrast microscopic image or a fluorescence microscopic image through an objective lens 6. In order to make an optical observation, the water-repelled substrate allows light transmission and the electrodes have translucency.

Figure 2:
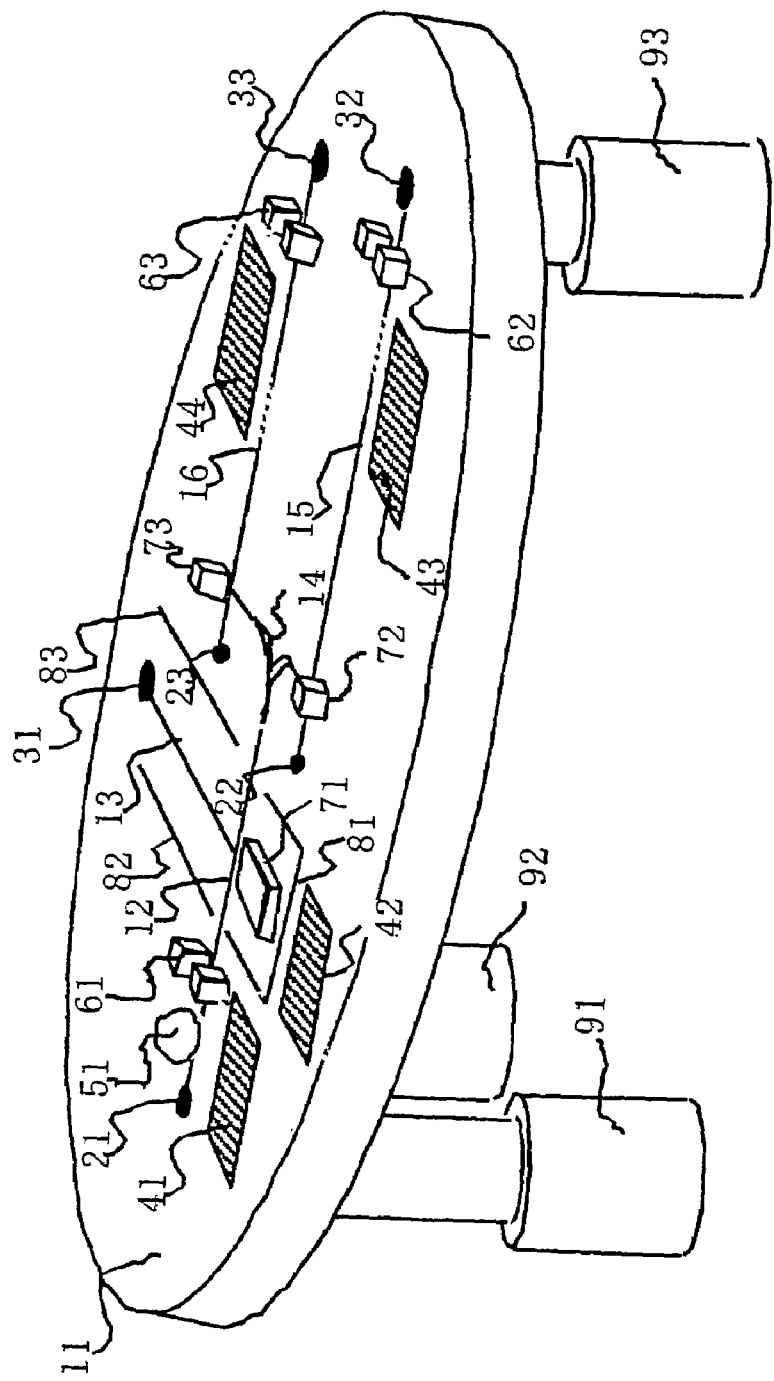
FIG. 2 is a pattern diagram illustrating an embodiment of the present invention.

An example of an actual measurement is explained with reference to the pattern diagram in FIG. 2.

A device explained in this embodiment includes a substrate 11 whose surface is subject to the water repellent treatment, solution intromission ports 21, 22 and 23 though which a test reagent or a droplet as a sample is introduced onto the substrate 11, grooves 12, 13, 14, 15 and 16 that when liquid is carried, roughly control an proceeding direction of the liquid, solution drain ports 31, 32 and 33 through which measured and fractionated droplet is taken out, electronic circuits 41 42, 43 and 44 for controlling elements on the substrate, optical measuring units 61, 62 and 63 for optically measuring the state of the droplet, electric field applying units 71, 72 and 73 for controlling the moving direction of a droplet 51, droplet guides 81, 82 and 83 for preventing the droplet from overriding, and legs of the substrate 91, 92 and 93. For example, the droplet 51 which is introduced from the solution intromission port 21 rolls over a gentle slope of the substrate 11 along the groove 12 and is introduced into the first optical measuring unit 61. An electric field is applied at an intersection between the groove 12 and the groove 13 by the electric field applying unit 71 according to the measured state of the droplet, so that the droplet is branched. When an electric field is not applied, the droplet proceeds to the next groove 14 at a branched passage, and when an electric field is applied, the droplet proceeds along the groove 13 to the solution drain port 31.

When the droplet 51 moves, the substrate 11 does not have to be slanted, and the moving speed can be controlled also by adjusting a width and a depth of the groove 12. As a matter of course, the speed may be controlled by arranging electrodes.

For example, the droplet which proceeds to the groove 14 at a branched passage proceeds to the groove 15 or the groove 16 by means of the electric field applying unit 72 or 73. While the droplet which proceeds to the groove 15 or the groove 16 is maintained in that place by the electric field applying unit 72 or 73, that droplet collides against a droplet introduced from the solution intromission port 22 or 23 so that they fuse. After the necessary reaction time passes, the droplet rolls again along the groove 14 or 15, and is measured by the optical measuring unit 72 or 73, so as to be recovered at the solution drain port 32 or 33. In this embodiment, the electric field applying units are arranged on the substrate, but as shown in FIG. 1, they may be arranged under the water-repelled surface of the substrate. Droplets to which positive or negative charges are applied or droplets to which electric charges are not applied may be introduced from the solution intromission ports 21, 22 and 23. In the embodiment, after a plurality of droplets are mixed, they are only optically measured, but the droplets may be further fractionated according to the optically measured result.

As a matter of course, the present invention is not limited to the above embodiments, and its details can be variously modified.

INDUSTRIAL APPLICABILITY

As detailed above, according to the present invention, small quantity of liquid containing cell, microbe, chemical substance or the like is operated as a droplet so as to be capable of being carried, mixed, observed and measured.

The invention claimed is:

1. A droplet operation device for biological and/or medical analysis comprising:
    an insulating substrate;
    a plurality of electrode units arranged on the insulating substrate, the electrode units for controlling movement and stoppage of a droplet;
    an insulating layer covering an upper surface of each of the electrode units, the upper surface being opposite to a lower surface of each of the electrode units that is in contact with the insulating substrate;
    a unit that supplies the droplet onto a surface of the insulating layer;
    a unit that applies an electric field to the electrode units so as to control the droplet on the surface of the insulating layer; and
    a unit that measures a state of the droplet, wherein
    the surface of the insulating layer is water repellent,
    the surface of the insulating layer has a groove, and
    the unit that supplies the droplet onto the surface of the insulating layer supplies the droplet to the groove on the surface of the insulating layer.

2. The droplet operation device according to claim 1, further comprising a unit that optically and telescopically measures an internal state of the droplet.

3. The droplet operation device according to claim 2, wherein the droplet contains a cell or a microbe.

4. The droplet operation device according to claim 1, further comprising a unit that measures absorbance of the droplet.

5. The droplet operation device according to claim 4, wherein the droplet contains a cell or a microbe.

6. The droplet operation device according to claim 1, further comprising a unit that measures fluorescence intensity of the droplet.

7. The droplet operation device according to claim 6, wherein the droplet contains a cell or a microbe.

8. The droplet operation device according to claim 1, further comprising a unit that mixes a plurality of droplets.

9. The droplet operation device according to claim 8, wherein the droplet contains a cell or a microbe.

10. The droplet operation device according to claim 1, wherein the droplet contains a cell or a microbe.

* * * * *